United States Patent [19]

Barberet et al.

[11] Patent Number: Plant 6,369

[45] Date of Patent: Nov. 1, 1988

[54] CARNATION VARIETY 'LONGOTOM'

[75] Inventors: Nicole Barberet; Yves Ducloux, both of Antibes, France

[73] Assignee: Laboratoire de Physiologie Vegetale de la Londe, La Londe, France

[21] Appl. No.: 890,374

[22] Filed: Jul. 29, 1986

[51] Int. Cl.[4] ..... A01H 5/00

[52] U.S. Cl. ..... Plt./71

[58] Field of Search ..... Plt./71

*Primary Examiner*—Robert E. Bagwill

*Attorney, Agent, or Firm*—Charles W. Rummler

[57] ABSTRACT

A new standard carnation cultivar particularly distinguished by its very large blooms having a light purple coloration, borne on long, strong, straight stems and which have a recurrent blooming habit with profuse production in the spring, midseason and fall but having a tendency to give less blooms in the fall. This plant has a vigorous, upright growth habit reaching a height of about one hundred centimeters at eight months with moderately abundant foliage, the flower stem having an average length of about eighty-two centimeters.

1 Drawing Sheet

BACKGROUND OF THE NEW PLANT

This new carnation cultivar originated as a seedling developed as the result of our breeding efforts carried on at La Londe, Les Maures, France, with the object of developing plants having blooms of attractive color and good quality on a plant having a strong resistance to *Fusarium oxysporum.* This seedling was selected from a group produced by our crossing of selected and individually identified plants growing among our stock of plants maintained at La Londe for breeding purposes, this particular seedling having been selected by us for propagation and test because of its very unusual flower color and its apparently very favorable growth habit. This discovery plant was reproduced by us at La Londe by means of cuttings with very satisfactory results and subsequently this plant was propagated in the same way through several successive generations, which demonstrated that the novel and distinctive characteristics of the discovery plant were fully retained from generation to generation and appeared to be firmly fixed.

DESCRIPTION OF THE DRAWING

This new carnation cultivar is illustrated by the accompanying photographic drawing which shows, in full color, a bud and several flowers in various stages of opening, the colors shown being as nearly true to those specified herein as is reasonably possible to obtain by conventional photographic procedures.

DESCRIPTION OF THE NEW PLANT

The following is a detailed description of our new carnation discovery based upon observations of greenhouse grown plants at La Londe, Les Maures, France, early in 1986, the color designations being specified according to The R.H.S. Colour Chart published by The Royal Horticultural Society at London, England.

THE PLANT

Origin: Seedling.

Parentage:

*Seed parent.*—Stock Plant No. 84 07 P (unnamed and unpatented).

*Pollen parent.*—Stock Plant No. 70 V 43 (unnamed and unpatented). These unnamed varieties are individually identified in our permanent records and are maintained for breeding purposes in our collection of carnation plants at La Londe, Les Maures, France.

Classification:

*Botanic.*—Hybrid *Dianthus caryophyllus.*

*Commercial.*—Standard Carnation.

Form: A tall, erect bush comprising at least four stems emitted near the ground from a main stem having a length of less than 15 cm. due to pinching.

Growth habit: Vigorous, upright and quite rigid.

Foliage:

*Quantity.*—Moderately abundant.

*Number of leaves.*—More than 120.

*Size of leaf (at 7th node).*—About 16.8 cm. long and about 1.2 cm wide, in average.

*Leaf shape.*—Linear, with rolled margins and an acuminate apex.

*Texture.*—Leathery.

*Color.*—Upper side — 189A. Under side — 189A.

*Ribs, veins and rachis.*—Hardly noticeable.

*Leaflets.*—There are no leaflets.

THE BUD

Form: Ovoid.

Size:

*Diameter.*—About 2.2 cm., in average.

*Length.*—About 3.2 cm., in average.

Rate of opening: About normal for carnations.

Color of petals:

*When sepals first divide.*—Rhodamine, 68D.

*When petals begin to unfurl.*—Spiraea Red, 63D.

Sepals: The sepals are joined at the lower part and the upper part is of ovate character with a sharp pointed apex.

*Number.*—Five. The sepals are hooded over the bud before dividing and when the flowers open, the sepals stand up.

*Color.*—Inside — 145D and 144D. Outside — 137D and 144C.

*Striae.*—Longitudinal.

Calyx: Generally bell shaped.

*Size.*—Large.

*Splitting.*—The calyx does not split.

*Aspect.*—Smooth.

Flower stem:

*Length.*—About 82 cm., in average.

*Character.*—Erect and rigid.

*Color.*—189A.

THE FLOWER

Blooming habit: Recurrent and profuse during spring, midseason and fall, with a tendency to give fewer blooms in fall.

Size: Very large.

*Diameter.*—About 9 cm., in average.

*Depth.*—About 6 cm., in average.

Borne: Singly.

Shape:

*When bloom first opens.*—High centered.

*When bloom matures.*—Generally ball shaped.

Petalage:

*Number.*—About 60, in average.

*Arrangement.*—Imbricated.

*Form.*—Fan shaped with rounded edges and with serrations at the outer ends.

*Texture.*—Leathery.

*Appearance.*—Satiny.

*Color.*—Both outside and inside petals: Body — 63D with 73C at the inner portions and end edges. Base — Greenish. Reverse side — 68D.

Petaloids:

*Number.*—Less than 10.

*Size.*—Smaller than the petals.

*Color.*—Substantially the same as the petals.

Flower stem:

*Length.*—Averaging about 82 cm. when cut at the tenth node.

*Character.*—Upright and of good strength.

*Color.*—189A.

Fragrance: Strong.

Persistence: The petals hang on and dry.

Disease resistance: Tolerant to *Fusarium oxysporum* as observed I.N.R.A. Antibes, France.

Lasting quality:

*As a cut flower.*—At least ten days in vase keeping.

REPRODUCTIVE ORGANS

Stamens:

Number.—Less than three arranged around the ovary.

*Anthers.*—Size: About 0.4 cm. Color: Whitish.

*Filaments.*—Length: About 2 cm., in average. Color: Whitish.

Pistils:

*Number.*—2 or 3.

*Styles.*—Length: About 2.7 cm. Color: Pinkish.

*Stigmas.*—Color: Pinkish.

Character of ovary: The ovary is ribbed.

This plant is somewhat similar to 'Londapo' (U.S. Plant Pat. No. 5,515) but differs by having a lighter color and a larger flower and with no splitting of the calyx.

We claim:

1. A new and distinct carnation cultivar, substantially as herein shown and described, characterized by the very large size of its flowers which are generally of a light Purple color with petals which are tinged at the inner body portion and outer end edges with a somewhat darker Mallow Purple color; the plant being further characterized by its recurrent and profuse production of flowers during its blooming seasons.

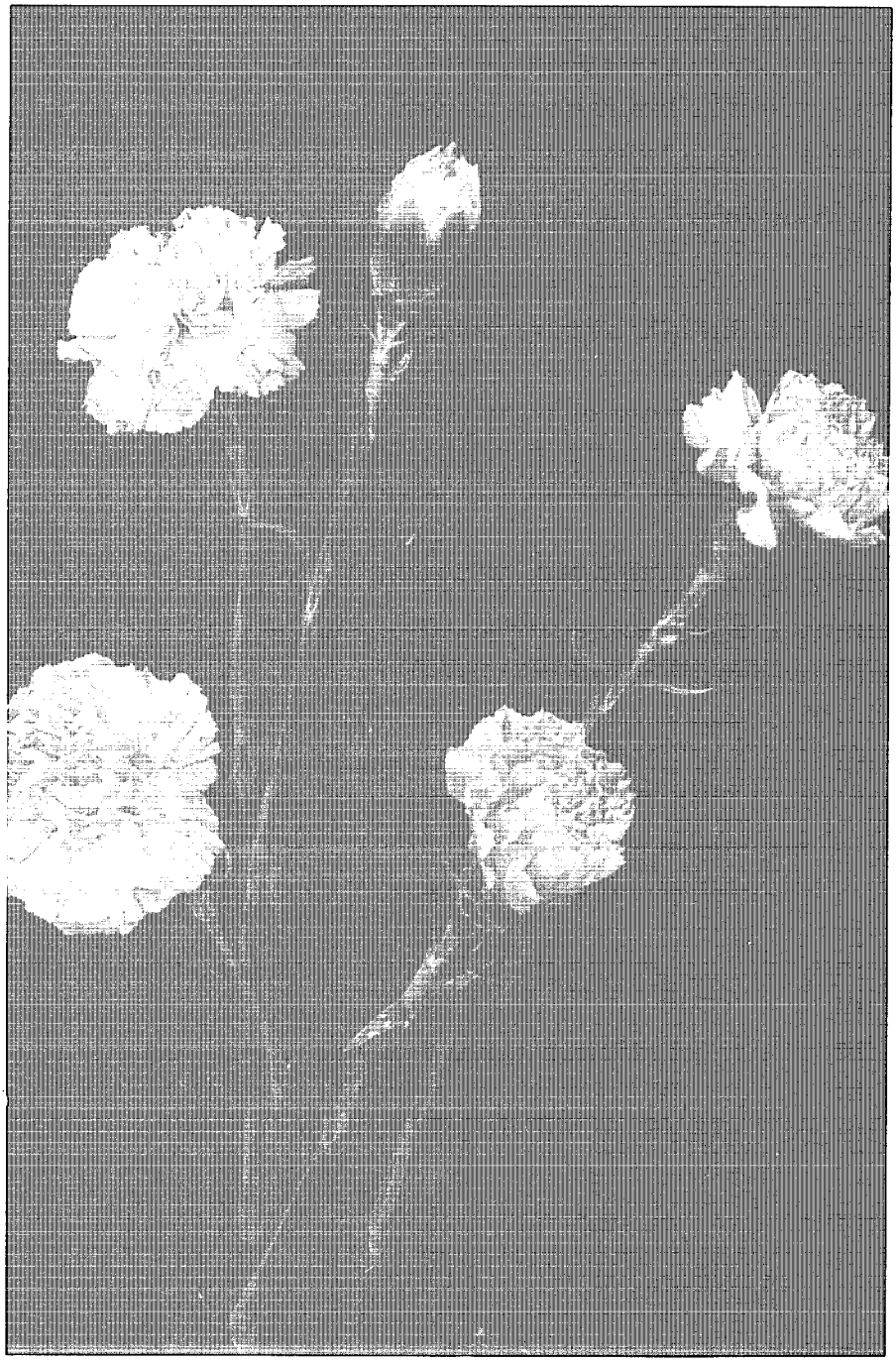

* * * * *